United States Patent
Blancke et al.

(10) Patent No.: US 10,617,826 B2
(45) Date of Patent: Apr. 14, 2020

(54) DRUG DELIVERY DEVICE WITH DOSE DELIVERY CLICKER

(71) Applicant: SANOFI-AVENTIS DEUTSCHLAND GMBH, Frankfurt am Main (DE)

(72) Inventors: Stefan Blancke, Frankfurt am Main (DE); Axel Teucher, Frankfurt am Main (DE); Michael Jugl, Frankfurt am Main (DE); Christiane Schneider, Frankfurt am Main (DE)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 827 days.

(21) Appl. No.: 15/036,529

(22) PCT Filed: Nov. 17, 2014

(86) PCT No.: PCT/EP2014/074701
§ 371 (c)(1),
(2) Date: May 13, 2016

(87) PCT Pub. No.: WO2015/074976
PCT Pub. Date: May 28, 2015

(65) Prior Publication Data
US 2016/0296706 A1    Oct. 13, 2016

Related U.S. Application Data

(60) Provisional application No. 61/907,475, filed on Nov. 22, 2013.

(30) Foreign Application Priority Data

Apr. 24, 2014    (EP) .................................. 14165745

(51) Int. Cl.
| | | |
|---|---|---|
| A61M 5/315 | (2006.01) |
| A61M 5/24 | (2006.01) |
| A61M 5/31 | (2006.01) |

(52) U.S. Cl.
CPC ............ *A61M 5/3157* (2013.01); *A61M 5/24* (2013.01); *A61M 5/3158* (2013.01);
(Continued)

(58) Field of Classification Search
CPC .......... A61M 5/3157; A61M 2205/581; A61M 2205/582; A61M 2205/583;
(Continued)

(56) References Cited

U.S. PATENT DOCUMENTS

| | | |
|---|---|---|
| 533,575 A | 2/1895 | Wilkens |
| 5,226,895 A | 7/1993 | Harris |

(Continued)

FOREIGN PATENT DOCUMENTS

| | | |
|---|---|---|
| EP | 0730876 | 9/1996 |
| EP | 0937471 | 8/1999 |

(Continued)

OTHER PUBLICATIONS

International Preliminary Report on Patentability in International Application No. PCT/EP2014/074701, dated May 24, 2018, 8 pages.

(Continued)

*Primary Examiner* — Brandy S Lee
*Assistant Examiner* — Hong-Van N Trinh
(74) *Attorney, Agent, or Firm* — Fish & Richardson P.C.

(57) ABSTRACT

An assembly for a drug delivery device is provided comprising a housing, and a lead screw having a longitudinal axis, a distal end and a proximal end, the lead screw being rotatably fixed during dose setting and dose delivery and axially movable in a distal direction relative to the housing, (Continued)

the lead screw further including a thread. The assembly further comprises a drive nut threadedly engaged with and screwable along the lead screw thread and a dial link connected with the drive nut and axially movable and rotatably fixed relative to the drive nut, where the dial link comprises a first portion of a feedback ratchet. The assembly is configured such that, during dose delivery, the assembly generates a feedback signal.

12 Claims, 5 Drawing Sheets

(52) U.S. Cl.
CPC .... *A61M 5/31528* (2013.01); *A61M 5/31551* (2013.01); *A61M 5/31585* (2013.01); *A61M 5/31593* (2013.01); *A61M 2005/3126* (2013.01); *A61M 2205/581* (2013.01); *A61M 2205/582* (2013.01)

(58) Field of Classification Search
CPC .......... A61M 2205/58; A61M 5/31571; A61M 5/31566; A61M 5/31565; A61M 5/31568; A61M 5/31541; A61M 2005/3126; A61M 5/20; A61M 5/31593; A61M 5/31535; A61M 5/31556; A61M 5/3156; A61M 5/24; A61M 5/31528; A61M 5/31551
See application file for complete search history.

(56) References Cited

U.S. PATENT DOCUMENTS

| | | | |
|---|---|---|---|
| 5,279,586 A | 1/1994 | Balkwill | |
| 5,304,152 A | 4/1994 | Sams | |
| 5,320,609 A | 6/1994 | Haber et al. | |
| 5,383,865 A | 1/1995 | Michel | |
| 5,480,387 A | 1/1996 | Gabriel et al. | |
| 5,505,704 A | 4/1996 | Pawelka et al. | |
| 5,582,598 A | 12/1996 | Chanoch | |
| 5,626,566 A | 5/1997 | Petersen et al. | |
| 5,674,204 A | 10/1997 | Chanoch | |
| 5,688,251 A | 11/1997 | Chanoch | |
| 5,921,966 A | 7/1999 | Bendek et al. | |
| 5,938,642 A * | 8/1999 | Burroughs ........ | A61M 5/31551 604/208 |
| 5,961,495 A | 10/1999 | Walters et al. | |
| 6,004,297 A | 12/1999 | Steenfeldt-Jensen et al. | |
| 6,193,698 B1 | 2/2001 | Kirchhofer et al. | |
| 6,221,046 B1 | 4/2001 | Burroughs et al. | |
| 6,235,004 B1 | 5/2001 | Steenfeldt-Jensen et al. | |
| 6,248,095 B1 | 6/2001 | Giambattista et al. | |
| 6,899,698 B2 | 5/2005 | Sams | |
| 6,936,032 B1 | 8/2005 | Bush, Jr. et al. | |
| 7,241,278 B2 | 7/2007 | Moller | |
| 2002/0052578 A1 | 5/2002 | Moller | |
| 2002/0120235 A1 | 8/2002 | Enggaard | |
| 2003/0050609 A1 | 3/2003 | Sams | |
| 2004/0059299 A1 | 3/2004 | Moller | |
| 2004/0210199 A1 | 10/2004 | Atterbury et al. | |
| 2004/0267207 A1 | 12/2004 | Veasey et al. | |
| 2005/0113765 A1 | 5/2005 | Veasey | |
| 2006/0153693 A1 | 7/2006 | Fiechter et al. | |
| 2009/0275916 A1 | 11/2009 | Harms et al. | |
| 2011/0092915 A1 | 4/2011 | Olson et al. | |

FOREIGN PATENT DOCUMENTS

| | | |
|---|---|---|
| EP | 0937476 | 8/1999 |
| JP | 2002-503116 | 1/2002 |
| JP | 2007-502146 | 2/2007 |
| JP | 2013-508032 | 3/2013 |
| WO | WO 96/27400 | 9/1996 |
| WO | 99/38554 | 8/1999 |
| WO | 01/10484 | 2/2001 |
| WO | 2005/018721 | 3/2005 |
| WO | WO 2005/018721 | 3/2005 |
| WO | 2008/083875 | 7/2008 |
| WO | 2011/003980 | 1/2011 |
| WO | WO 2011/047298 | 4/2011 |

OTHER PUBLICATIONS

International Search Report and Written Opinion for Int. App. No. PCT/EP2014/074701, dated Apr. 8, 2015.

* cited by examiner

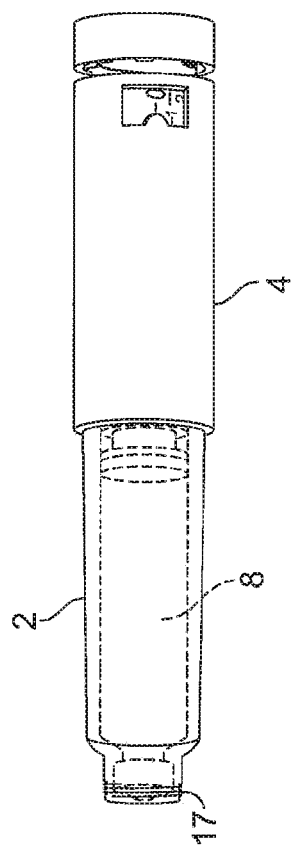
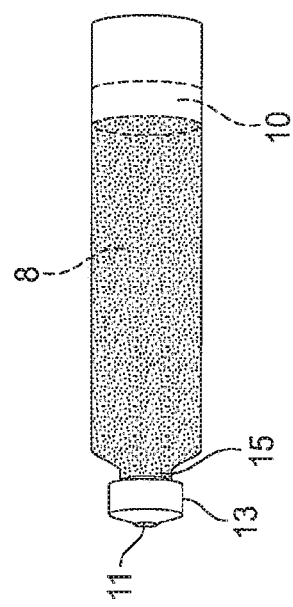
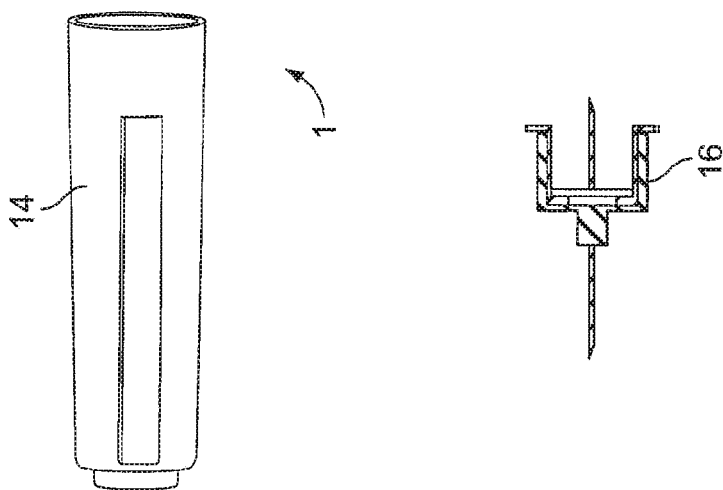
FIG. 1
FIG. 2

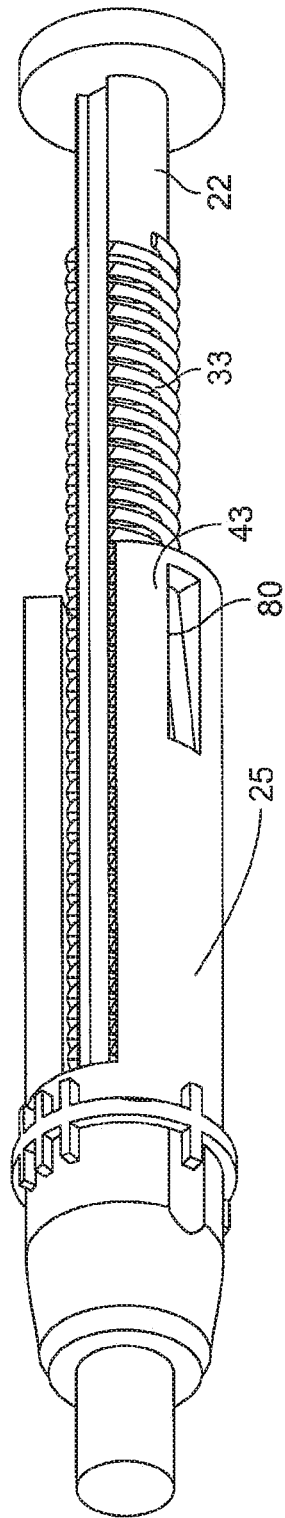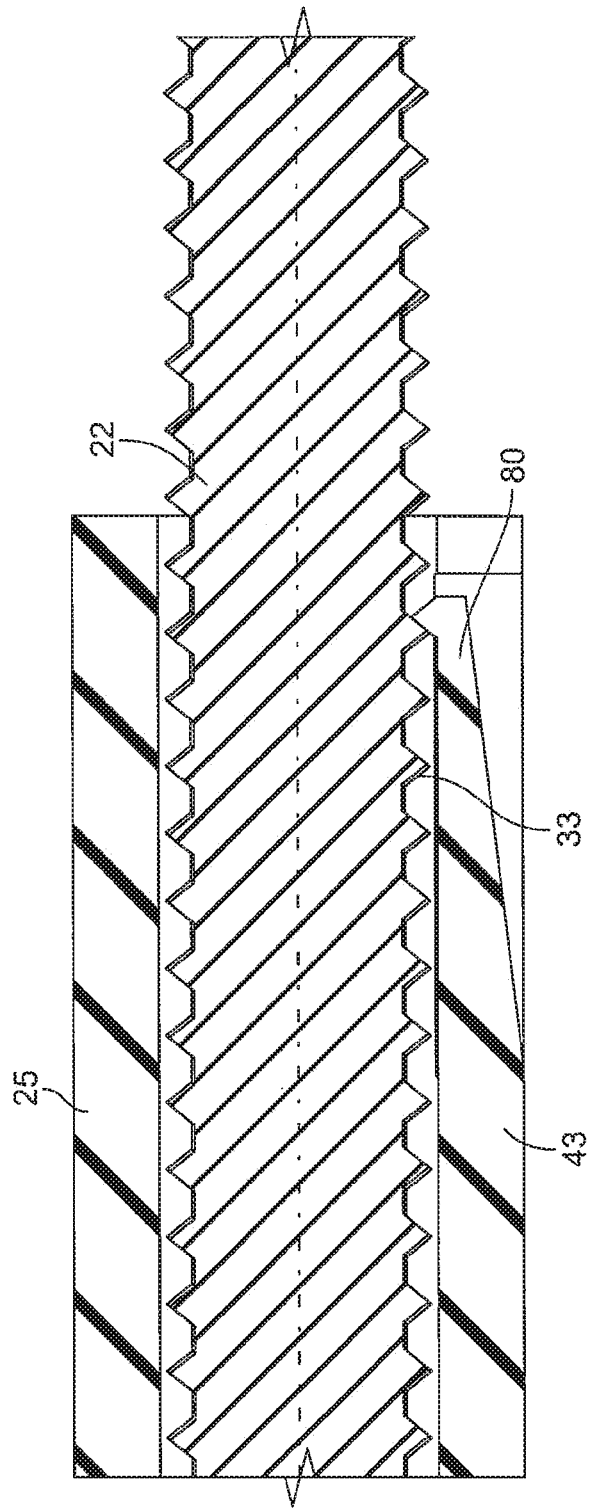

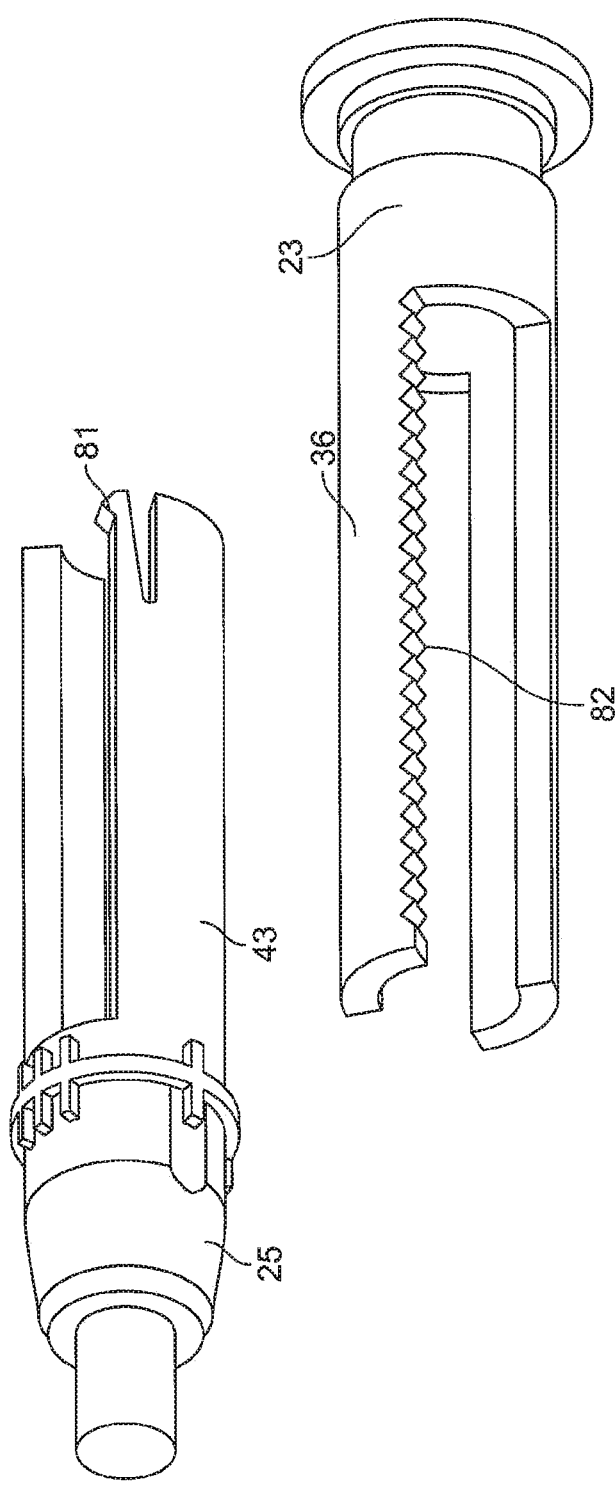
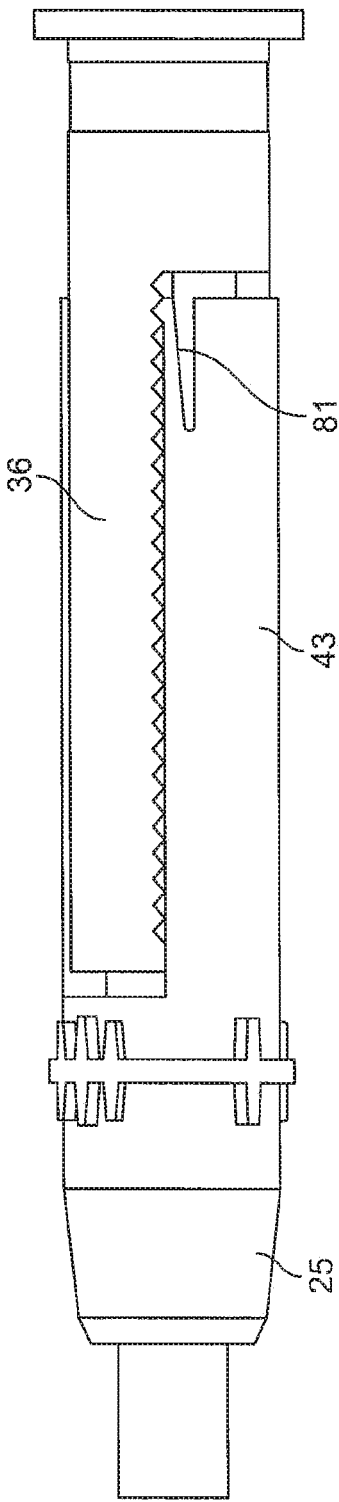

DRUG DELIVERY DEVICE WITH DOSE DELIVERY CLICKER

CROSS REFERENCE TO RELATED APPLICATIONS

The present application is a U.S. National Phase Application pursuant to 35 U.S.C. § 371 of International Application No. PCT/EP2014/074701 filed Nov. 17, 2014, which claims priority to U.S. Provisional Patent Application No. 61/907,475 filed Nov. 22, 2013 and European Patent Application No. 14165745.2, filed Apr. 24, 2014. The entire disclosure contents of these applications are herewith incorporated by reference into the present application.

TECHNICAL FIELD

The present patent application is generally directed to drug delivery devices, such as pen-type injection devices, and preferably to the dose setting and dose delivery mechanisms for such drug delivery devices. Such devices provide for self-administration of medicinal product from a multi-dose cartridge and permit a user to set the delivery dose. The present application may find application in both disposable and reusable type drug delivery devices. However, aspects of the invention may be equally applicable in other scenarios as well.

BACKGROUND

Drug delivery devices have application where regular injection by persons without formal medical training occurs. This is increasingly common among patients having diabetes where self-treatment enables such patients to conduct effective management of their disease. Diabetes has been shown to cause certain problems. For example, people with diabetes can get high blood pressure, kidney disease, nerve damage, heart disease, and even in certain circumstances blindness. The damage caused by these problems may occur in patients whose blood sugar has been out of control for years. Keeping blood sugar under control, by way of effective insulin administration, is one method that can help prevent this damage from occurring.

In addition, people with diabetes can go into "diabetic coma" if their blood sugar is too high. They can also develop blood sugar that is too low (i.e. hypoglycemia) if they don't get enough food, or they exercise too much without adjusting insulin or food. Both diabetic coma and hypoglycemia can be very serious, and even fatal, if not treated quickly. Closely watching blood sugar, being aware of the early signs and symptoms of blood sugar that is too high or too low, and treating those conditions early can prevent these problems from becoming too serious.

Pen type drug delivery devices have been designed and developed to help patients suffering from diabetes and other disease states so as to prevent such problems from occurring. The circumstances identified above highlight a number of design considerations and criteria for drug delivery devices, especially those that may be used to treat diabetes. As just one example, one requirement is that the drug delivery device must be robust in construction. The drug delivery device must also be easy to use both in terms of the drug delivery device manipulation and understanding of the device's operation. Diabetics, for instance, have to inject themselves repeatedly with insulin solution and the volume of insulin to be injected may vary from patient to patient and even from injection to injection. For at least this reason, certain diabetics may require drug delivery devices that allow the patient to inject successive measured dosages of the same or perhaps different preset volumes of insulin solution accurately and with minimum dexterity challenges. This presents a further design challenge since, in the case of certain diabetics, users may have impaired vision and/or may be physically infirm with limited dexterity.

Generally, drug delivery and/or injection devices include a cartridge having a slidable piston and containing a multi-dose quantity of liquid medication. A lead screw extending from the dose setting mechanism of the injector pen is movable in a forward (i.e., distal direction) to advance the piston within the cartridge in such a manner as to dispense the contained medication from an outlet at the opposite cartridge end, typically through a needle that penetrates a stopper or septum at that opposite end. In disposable or prefilled pens where the cartridge is permanently sealed within the pen housing, after a pen has been utilized to exhaust the supply of medication within the cartridge, the entire pen is then discarded. In reusable pens, after a pen has been utilized to exhaust the supply of medication within the cartridge, the pen is disassembled to allow replacement of the spent cartridge with a fresh cartridge, and then the pen is reassembled for its subsequent use.

A number of injection devices are commercially available and unfortunately a number of those devices suffer from one or more design flaws that may result in the improper use of the injection device or the delivery of an inaccurate dosing of the medicament. Inaccurate dose setting could lead to fatal results. Other design flaws allow the possibility that a counterfeiter can dissemble a disposable pen and insert bogus medicament cartridge. This pen is then reassembled and sold as new. In some cases, the initially designed device does not provide feedback to a user during dispensing of the preset dose or at the completion of the dose. For the users who are visually and/or hearing impaired the ability to receive audible or tactile feedback is very important in order that the user hears or feels that the preset dose is being delivered and importantly that the injection is completed. Knowledge of the completion of the injection is very important to ensure a proper delivery of medicament is performed because users are taught to leave the injection needle in the skin for 10 seconds at the end of dosing to make sure all of the medicament is delivered. Without such feedback features the risk of an improper injection being performed or under dosing is greatly increased, especially if the user dose not know when to begin the 10 second countdown. Such design flaws may not be realized when a pen is first commercialized and may only become apparent after the injection device has been in commercial use by patients for an extended period of time. As such, there exists a need to evaluate existing pen designs to identify the design flaws and then take corrective action, which typically would include redesigning certain original mechanisms within the injection device.

A pen injector lending itself to design improvements is described in WO 2005/018721.

SUMMARY

It is an object of the present disclosure to present an assembly for a drug delivery device, by which assembly the drug delivery device, such as a pen-type device, can be improved.

This object is achieved by the subject-matter of the independent claim. Advantageous embodiments and refinements are subject-matter of the dependent claims.

One aspect of the present disclosure relates to an assembly for a drug delivery device comprising a housing and a lead screw having a longitudinal axis, a distal end and a proximal end, wherein the lead screw is rotatably or rotationally fixed during dose setting and dose delivery and axially movable in a distal direction relative to the housing. Preferably, the longitudinal axis extends from the distal end to the proximal end of the lead screw. The longitudinal axis may coincide or be directed parallel to a longitudinal axis of the housing and/or the drug delivery device.

A further aspect of the present disclosure relates to a drug delivery device comprising the assembly.

Dose setting and/or dose delivery shall relate to a dose setting operation, in which a dose of drug to be dispensed from the device is set, and a dose delivery or dose dispensing operation, in which the set dose or another dose is delivered or dispensed from the device, respectively. Preferably, during dose setting and dose delivery the lead screw is not movable in a proximal direction relative to the housing.

The lead screw further includes or comprises a thread, such as a helical thread.

The assembly further comprises a drive nut which is threadedly engaged with, and e.g. screwable along, the thread of the lead screw (lead screw thread).

The assembly further comprises a dial link which is connected with the drive nut and axially movable and rotatably or rotationally fixed relative to the drive nut, wherein the dial link comprises a first portion of a feedback ratchet. The feedback ratchet is preferably disposed to provide an audible and/or tactile feedback to the user during an operation of the assembly and/or the drug delivery device. Preferably, the feedback ratchet provides a feedback particularly during dose dispensing and/or dose delivery.

In an embodiment, during dose delivery, the dial link and the drive nut are not rotated with respect to the housing. Such an embodiment facilitates and or enables the general concept of the assembly and/or the drug delivery device.

The assembly is configured such that, during dose setting, the dial link is moved relative to the housing a first axial distance from a home position and the drive nut is moved along the thread a second axial distance that is e.g. different from the first axial distance. Preferably, the first axial distance is greater than the second axial distance. Moreover, the dial link as well as the drive nut may, at the same time, be rotated relative to the housing in the same rotational direction. The home position is preferably a position of the dial link relative to the housing originating from which a dose setting operation may start and/or a position in which the dial link is repeatedly arranged after a dose delivery and/or before a dose setting operation during the operational lifetime of the assembly and/or the device.

The assembly is further configured such that, during dose delivery, the dial link is moved relative to the housing back towards the home position and the drive nut, and therewith the lead screw, is advanced axially, preferably in order to dispense a dose of drug from the device. In this way, the device and/or the assembly may comprise a piston which may be arranged in a cartridge of and/or distally beside the lead screw such that an axial, preferably a distal, advance of the lead screw also advances the piston in the cartridge in order to dispense or deliver a dose of drug from the device. Said advancement may relate to an axial, such as a proximal movement of the lead screw, for example. Further, said advancement preferably relates to a movement of the lead screw for the second axial distance.

The assembly further comprises a second portion of the feedback ratchet, wherein the second portion is arranged and configured to engage the first portion such that, during dose delivery, the contact between said portions generates a feedback signal to the user. In the same way, the first portion may be configured to engage the second portion or both portions may be configured to engage each other. Said feedback signal may be an audible and/or a tactile one, as mentioned above.

In an embodiment, the feedback ratchet is a clicker ratchet or clicker feedback mechanism.

Advantageously, the present assembly provides an improved feedback to the user, especially during dose dispensing as e.g. a feedback signal which may, besides the information that a dose is currently being delivered, inform the user about a filling state of the cartridge. This may allow the user to distinguish e.g. between a clicker mechanism or feedback which may be provisioned for setting of a dose from the respective feedback during a dose delivery.

In an embodiment, the second portion is arranged and configured to engage the first portion such that, during dose setting, the contact between said portions generates a separate feedback signal to the user. This embodiment or functionality is expediently and advantageously provisioned along with the embodiment described herein, wherein during dose delivery the signal is generated.

In an embodiment, one of the first and the second portion of the feedback ratchet comprises a ratchet arm configured to engage the respective other portion of the feedback ratchet. Via the ratchet arm, the feedback signal generated by the engagement, interaction or cooperation of the first and the second portion of the feedback ratchet, may be established or facilitated in an expedient way.

In an embodiment, the assembly is configured such that, during dose dispensing and/or dose delivery, the onset of the feedback signal depends on the actual advancement of the lead screw with respect to the housing. According to this embodiment, the feedback or feedback signal may be designed such that an information about the filling status of the assembly or the device and/or about the current setting and/or delivery state may be provided to the user.

In an embodiment, the assembly is configured such that the distance by which the dial link is moved axially relative to the lead screw during dose setting is different from the distance by which the dial link is moved axially relative to the lead screw during delivery of the set dose. This embodiment may be necessary and/or advantageous for the functioning of the device, wherein the lead screw is preferably not movable in the proximal direction during an operation of the device. Said operation may relate to a dose setting and/or dose delivery. As, the lead screw is expediently moved distally with respect to the housing and the dial link during dose delivery, the relative movement between the lead screw and the dial link is greater during dose setting. This effect may be exploited to establish a feedback during dose setting which differs audibly and/or tactilely from the feedback produced or generated during dose dispensing. Thereby, in turn, an additional safety measure is provided in that, the user is informed which kind of operation of the device is actually being performed. Expediently, the axial distance of relative movement of the dial link and the lead screw during setting is greater than the axial distance of relative movement of said components during dose delivery.

In an embodiment, the assembly is configured such that the lead screw is not moved axially during dose setting, and, during dose setting, the first portion and the second portion of the feedback ratchet only initially interact.

In an embodiment, the assembly is configured such that, during dose delivery, the first portion and the second portion do not engage or interact in a first time interval, wherein said portions do interact in a subsequent second time interval.

Said time intervals may be determined by the distance that the lead screw has already been advanced, e.g. with respect to the housing during the operational lifetime of the assembly and/or the device.

In other words, during dose delivery, the first portion and the second portion may only interact within a terminal fraction of relative axial movement of said portions as, e.g. in an initial fraction, which may correspond to the mentioned first time interval, the components respectively comprising the first and the second portion may—depending on the operational state—not overlap axially, although the device is operable.

In an embodiment, the drive nut comprises the second portion of the feedback ratchet. As the drive nut, due to the difference or dimensioning of the mentioned first axial distance and the second axial distance, expediently axially moves with respect to the dial link or vice versa, the feedback ratchet may, according to this embodiment, also be expediently established.

In an embodiment, the thread of the lead screw forms the second portion and the ratchet arm forms the first portion.

In an embodiment, the assembly is configured such that, during dose delivery, the lead screw is displaced distally relative to the first portion of the feedback ratchet, such that with increasing number of performed delivery actions, the onset of the delivery feedback shifts towards the end of the delivery action. According to this embodiment, a user may be notified about a filling state of the assembly and/or the device may be during an operation, for example.

In an embodiment, the drive nut comprises the second portion of the feedback ratchet.

In an embodiment, either the first portion comprises the ratchet arm and the second portion comprises a row, such as e.g. a linear row of ratchet teeth or the second portion comprises the ratchet arm and the first portion comprises the row of ratchet teeth.

In an embodiment, the portion of the first and the second portion, not comprising the ratchet arm, comprises a single ratchet tooth, wherein the first and the second portion are positioned such that only one end-of-dose feedback signal is generated when a set or preset dose is or has been fully or completely dispensed from the device. The said end-of-dose feedback or feedback signal may advantageously increase the safety of the assembly or the device, as the user of the device may not be tempted to stop dispensing of a dose, for example, even if said dose is not yet fully dispensed.

In an embodiment, the assembly comprises a number sleeve which is threadedly engaged with the housing. In this way, each of the number sleeve and the housing preferably comprise a thread, wherein the thread of the housing is preferably an inner thread, while the number sleeve thread is an outer thread. Preferably the number sleeve dose comprises indicia indicating e.g. the current dose setting and/or dose delivery state to the user. Moreover, the number sleeve may be arrangable in or according to the above-mentioned home position, preferably in the same manner as explained above by means of the dial link.

The assembly is further configured such that, during dose setting, the dial link is rotatably or rotationally fixed with or with respect to the number sleeve when the dial link and the number sleeve are in a first axial arrangement, and, during dose delivery, the number sleeve is rotatable relative to the dial link when the dial link and the number sleeve are in a second axial arrangement.

In an embodiment, the assembly comprising an inner sleeve, wherein the inner sleeve is axially fixed relative to the drive nut.

In an embodiment, the inner sleeve is rotatably fixed with respect to the housing.

In an embodiment, the inner sleeve is threadedly engaged with the number sleeve. Preferably, the inner sleeve comprises an outer thread and the number sleeve comprises an inner thread, accordingly. The assembly is further configured such that, during dose delivery, the inner sleeve advances the drive nut axially, such as proximally, in order to dispense a dose of drug, for example.

In an embodiment, the inner sleeve comprises the second portion of the feedback ratchet, wherein either the first portion comprises a ratchet arm and the second portion comprises a linear row of ratchet teeth or the second portion comprises a ratchet arm and the first portion comprises a linear row of ratchet teeth, expediently in order to generate the feedback signal.

In an embodiment, the first portion comprises a ratchet arm and the second portion comprises a linear row of ratchet teeth.

In an embodiment, the second portion comprises a ratchet arm and the first portion comprises a linear row of ratchet teeth.

In an embodiment, the assembly is configured such that a setting feedback clicker mechanism is established between the inner sleeve and the drive nut during dose setting, wherein, then, i.e. during dose setting, the setting feedback clicker mechanism generates a further feedback signal to the user. Said further feedback signal may be provisioned additionally or alternatively to the above-mentioned feedback signal and/or ratchet feedback. In this way, the type of feedback which is actually or efficiently given to the user during an operation of the device or the assembly, may advantageously vary or differ depending on whether a dose is set or dispensed. In particular, this may be case as the feedback signal of the feedback ratchet may interfere with the further feedback produced by the setting feedback clicker mechanism during setting of a dose.

In an embodiment, the threading of the number sleeve to the housing is of a first lead, the threading of the inner sleeve to the number sleeve is of the second lead, and the threading of the lead screw is of a third lead, and the first lead, the second lead and the third lead are not equal or differ. In this way, it may be expediently facilitated that e.g. the first axial distance and the second axial distance as mentioned above, are different as well as that the assembly and/or the device function in an expedient and easy way, whereby—at the same time—the presented feedbacks can be generated.

The following describes a number of design flaws and presents corrective solutions to eliminate these flaws. Additional aspects or information is further given in the following, wherein the set forth aspects are to be interpreted optionally and not necessarily to be essential for the present disclosure.

Drug delivery devices are designed to allow for self-administration of medicament in preset doses by the patient suffering from one or more disease states. Depending on the treatment regime set by the caregiver, a patient may have to perform self-injections several times a day. For this reason, pen type devices must be designed for all types of users, including the very young and the very old who may suffer from poor vision or hearing or manual dexterity. It is imperative therefore that the design of the injection device provide some type of feedback system to indicate to the user/patient that the injection is progressing correctly and that the injection is complete. For example, if there is no end of dose feedback signal provided, whether by a "CLICK" or the absence of clicking, the user may inadvertently stop the injection process before the required full dose is delivered. This of course would lead to under dosing, which in some disease states could be very dangerous to the user.

A physical examination of the commercial pen injection device that is generally described in WO 2005/018721 A1 reveals a design flaw in that the user is not provided any feedback that the set dose of medicament is being injected. To solve this problem, the present disclosure, particularly as described above—modifies the original design of the dosing mechanism to provide the user with a clicking feedback signal as the injection proceeds. Absence of the clicking signal indicates to the user that the injection is complete and that user should begin the 10-second hold time before the needle is removed. Two or more possible design changes are set forth. In one case the dial link is modified to engage the screw threads on the lead screw such that as the lead screw is pushed distally during injection the threads will engage and disengage a flexible arm on the fingers of the dial link causing a clicking sound. A second design change involves modifying both the dial link and the drive nut such that the relative axial movement of these parts during injection generates an audible clicking sound. This is accomplished by having a flexible arm on one of the dial link and drive nut that interacts with ratchet type teeth on the other part. A preferred approach is having the flexible arm or finger located on the distal end of the dial link and having a linear row of ratchet teeth on drive nut. In both embodiments, as described in more detail below, during dose delivery as the lead screw or drive nut is pushed distally the dial link spring or ratchet arm will ride up (flexing radially outward) and over (snapping back to position) each lead screw thread or ratchet tooth, respectively. This flexing and snapping back of the spring arm generates a "CLICK" noise and can also generate a tactile feedback signal to the device user that the injection is proceeding. The spacing between ratchet teeth can be chosen such that each click signifies one unit dose of medicament delivered. The pitch of the threads on the lead screw is already proportional to a unit dose of medicament.

The drug delivery device including the above described design improvement includes a housing, a lead screw having a threaded shaft that is rotatably fixed during dose setting and injecting and that only moves axially in a distal direction relative to the housing during dose administration and that is always prevented from moving proximally. The device also has a fluid container or cartridge defining a medicine-filled reservoir with a movable piston at one end and an outlet at the other end, where the piston is engaged by a bearing connected to the distal end of the lead screw. The piston is advanced toward the outlet or distal end of the cartridge when the lead screw is moved distally during dose administration.

A drive nut is threadedly engaged with the threads on the lead screw and can rotate and move proximally relative to the lead screw and housing during dose setting. A number sleeve is threadedly engaged with the housing and is screwed outwardly in the proximal direction relative to the housing during dose setting. A dial link is slidably and rotationally engaged with the drive nut and is axially movable and rotatably fixed relative to the drive nut. The dial link is rotatably fixed with the number sleeve through a clutch when the dial link and number sleeve are in a first axial arrangement and when in a second axial position the clutch, and hence the number sleeve, are disengaged from the dial link and the dial link becomes rotatable relative to the number sleeve. An inner sleeve is threadedly engaged with the number sleeve, were the inner sleeve is axially movable but rotatably fixed relative to the housing. During dose setting, the dial link and the number sleeve are in the first axial arrangement, whereby a screwing motion of the dose knob that is connected to the dial link and number sleeve relative to the housing screws the dial link and the number sleeve a first axial distance from a home position causing the number sleeve to extend in the proximal direction outwardly from the housing or body of the device. The screwing motion of the dial link screws the drive nut along the lead screw threaded shaft a second axial distance different than the first axial distance.

During dose dispensing, the dial link and the number sleeve element are in the second axial arrangement, whereby a screwing motion of the number sleeve relative to the housing back or inward toward the home position advances the inner sleeve without rotation in the distal direction to axially advance the drive nut and thereby the lead screw and the fluid container piston to dispense medicine from the outlet. The pen injector disclosed herein can be provided with a mechanical advantage that makes it easier for the user to push the dose knob during the dispensing of medication, which mechanical advantage can be very high and conveniently selected by the manufacturer during apparatus or device designing. This mechanical advantage allows the number sleeve to travel a greater axial distance than the lead screw advances, thus allowing for small doses to be delivered.

The present disclosure may further relate to the following aspects:

1. A drug delivery device comprising:

a housing;

a lead screw having a longitudinal axis, a distal end and a proximal end that is rotatably fixed during dose setting and dose delivery and axially movable in a distal direction relative to the housing, the lead screw including helical threads and a bearing foot connected to the distal end, wherein the lead screw has a keyway positioned parallel to the longitudinal axis;

a cartridge with a movable piston at one end and an outlet at the other end, the piston engagable by the lead screw bearing foot to be advanced toward said outlet when the lead screw is moved distally;

a drive nut threadedly engaged and screwable along the lead screw threaded shaft;

a number sleeve threadedly engaged with the housing to be screwable relative to the housing;

a dial link connected with the drive nut and axially movable and rotatably fixed relative to the drive nut, the dial link rotatably fixed with number sleeve when the dial link and number sleeve are in a first axial arrangement, the number sleeve rotatable relative to the dial link when the dial link and number sleeve are in a second axial arrangement, where the dial link comprises a first portion of feedback ratchet;

an inner sleeve threadedly engaged with the number sleeve, the inner sleeve axially movable and rotatably fixed relative to the housing;

a mid-body axially fixed inside of the housing, the mid-body including tabs that slidably fit within a keyway in the lead screw to prevent rotation of the lead screw within the housing;

wherein the inner sleeve is axially movable and rotatably fixed relative to the mid-body by at least one lug of the mid-body that slidably fits within at least one slot formed in the inner sleeve; and wherein the threading of number sleeve to the housing is of a first lead, the threading of the inner sleeve to the number sleeve is of a second lead, and the threading of the lead screw threaded shaft is of a third lead, and the first lead, the second lead and the third lead are not equal;

wherein during dose setting, the dial link and the number sleeve are in the first axial arrangement, whereby a screwing motion of dial link and number sleeve relative to the housing screws the dial link and the number sleeve a first axial distance from a home position, which screwing motion of dial link screws said drive nut along the lead screw threads a second axial distance that is different than the first axial distance;

wherein during dose delivery, the dial link and number sleeve are in said second axial arrangement, whereby a screwing motion of the number sleeve relative to the housing back toward the home position advances the inner sleeve without rotation in the distal direction to axially advance the drive nut that is axially fixed to the inner sleeve and thereby the lead screw and the movable piston to dispense fluid from the cartridge outlet.

2. The drug delivery device of aspect 1 where the first portion of the feedback ratchet comprises a ratchet arm configured to engage a section portion of the feedback ratchet comprising the helical threads on the lead screw or ratchet teeth on the drive nut.

3. The drug delivery device of aspect 2 where the ratchet arm is positioned radially inward and engages the threads on the lead screw such that during dose setting and dose delivery the contact between the ratchet arm and the threads generates a feedback signal to the user.

4. The drug delivery device of aspect 1 where the drive nut comprises a second portion of the feedback ratchet that cooperates with the first portion such that the cooperation generates a feedback signal to the user.

5. The drug delivery device of aspect 4 where the first portion comprises a ratchet arm and the second portion comprises a linear row of ratchet teeth.

6. The drug delivery device of aspect 4 where the second portion comprises a ratchet arm and the first portion comprises a linear row of ratchet teeth.

7. The drug delivery device of aspect 4 where the first portion comprises a ratchet arm and the second portion comprises a single ratchet tooth, where the first and second portions are positioned such that an end of dose feedback signal is generated when the a preset dose is fully dispensed.

These as well as other advantages of the various aspects of our improved assembly and/or drug delivery device, and the manner of attaining them, will become apparent to those of ordinary skill in the art by reading the following detailed description, with appropriate reference to the accompanying drawings.

BRIEF DESCRIPTION OF THE DRAWINGS

Exemplary embodiments are described herein with reference to the drawings, in which:

FIG. 1 is an illustration of one embodiment of the present invention showing the assembled pen type medication dispensing apparatus where the cap has been removed to reveal the cartridge container affixed to the dose setting mechanism;

FIG. 2 is close up view of the cartridge container and the pen needle that is attached to the cartridge container for injection of the medicament;

FIG. 5 is a perspective view of showing the interaction of the dial link and lead screw from the embodiment shown in FIG. 4;

FIG. 6 is a close-up cross-sectional view of the interaction of the dial link and lead screw from the embodiment shown in FIG. 4;

FIG. 7 is a perspective view of the dial link and drive nut from another embodiment of the invention; and FIG. 8 is a side view of the embodiment shown in FIG. 7 illustrating the interaction of the flexible arm on the dial link with the linear arrangement of ratchet teeth on the drive nut.

Figure 3:
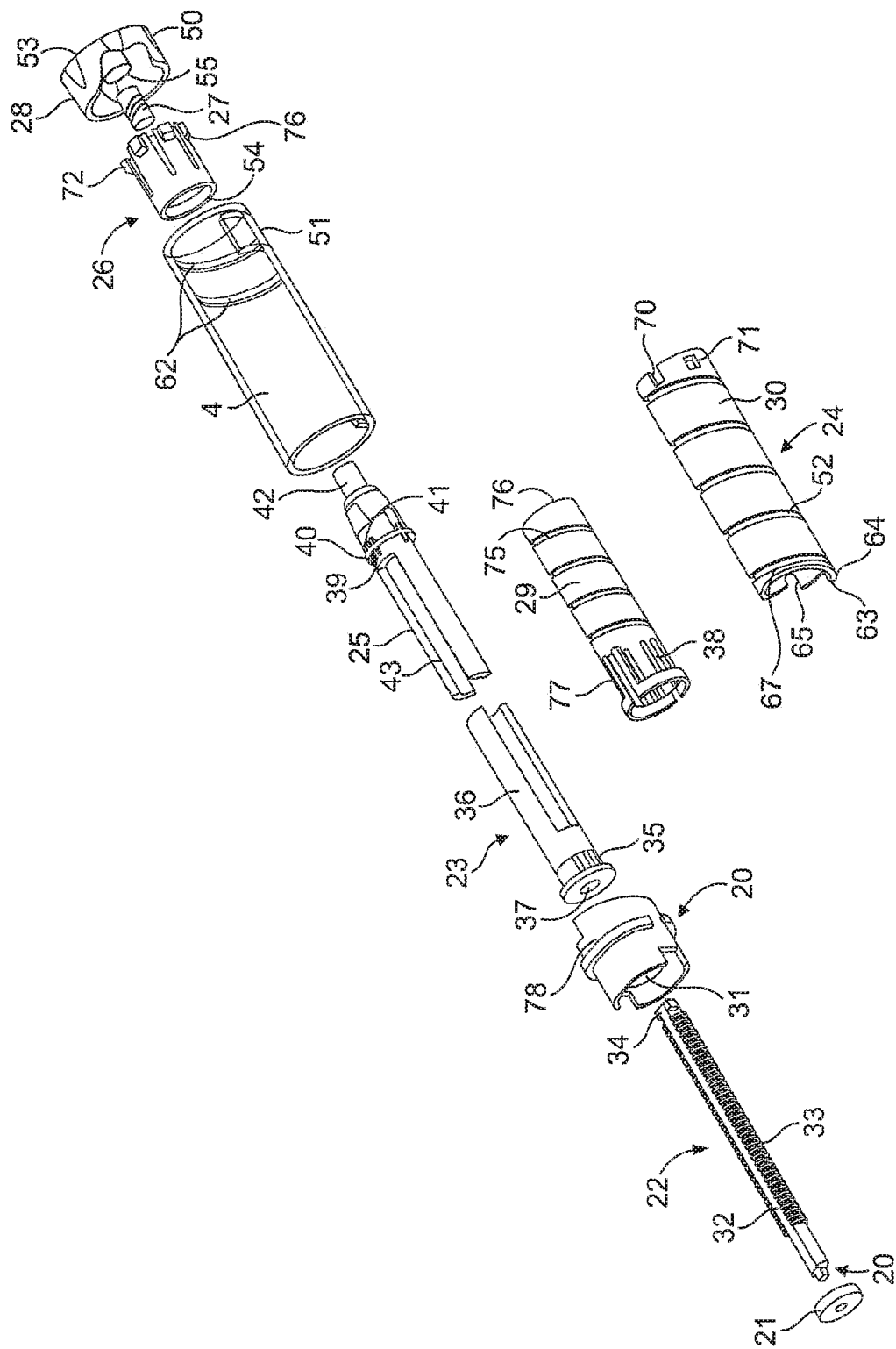
FIG. 3 is an exploded view of the embodiment from FIG. 1 showing each of the individual parts arranged relative to each other as they exist in the fully assembled device.

Corresponding reference characters indicate corresponding parts throughout the several views. Although the drawings represent embodiments of the present invention, the drawings are not necessarily to scale, and certain features may be exaggerated or omitted in some of the drawings in order to better illustrate and explain the present invention.

DETAILED DESCRIPTION

Referring first to FIGS. 1 to 3, there is shown a drug delivery device 1 as an injector pen, which pen has an elongated, substantially writing instrument-like form, although other forms are within the scope of the invention. The drug delivery device 1 may be a pen-type device. The drug delivery device 1 comprises a housing having a cartridge holder 2, and main (exterior) body or housing 4. The numeral 1 may as well indicate an assembly or parts thereof, wherein single or all of the parts or components of the device may relate or be comprised by the assembly. Reference to the injector or device may actually additionally or alternatively relate to the assembly for said device.

The drug delivery device 1 and the housing have a distal end and a proximal end. The term "distal end" designates that end of the drug delivery device 1 or a component thereof which is or is to be arranged closest to a dispensing end of the drug delivery device 1. The term "proximal end" designates that end of the device 1 or a component thereof which is or is to be arranged furthest away from the dispensing end of the device 1. The distal end and the proximal end are spaced apart from one another in the direction of an axis. The axis may be the longitudinal axis or rotational axis of the device 1.

The proximal end of the cartridge holder 2 and the distal end of the main housing 4 are secured together by appropriate retaining features depending on whether the pen injector is designed as a reusable device or as a disposable device. In the latter case, the retaining feature would be permanent using the connection means described below. If the device is reusable, the retaining meaning would be a screw-type connection, a Luerlok, snap fit, bayonet, or the like type or combination of fittings that allow the user to easily disassemble the device to replace the empty cartridge with a fresh new cartridge. In this illustrated arrangement, the cartridge holder 2 is secured within the proximal end of the main body 4.

A cartridge 8 from which a number of doses of a medicinal product may be dispensed is provided in the cartridge holder 2. Preferably, the cartridge 8 contains a type of medicament that must be administered often, such as once or more times a day. One such medicament is insulin. A piston 10 shown in FIG. 2 is initially retained in the proximal end of the cartridge 8 and as each injection is completed gradually moves distally to the empty cartridge position. A removable cap 14 is releasably retained connected to the main body 4 covering the cartridge holder 2.

The dose setting mechanism or the assembly of or for the drug delivery device illustrated in FIGS. 1-3 may be utilized as or for either a disposable or reusable drug delivery device. Where the drug delivery device 1 comprises or exhibits a disposable drug delivery device, the cartridge 8 cannot be removed from the device 1 without destroying the device. In a disposable device, the proximal end of the cartridge holder can be fixedly mounted or secured, via adhesives, ultrasonic welding or in another suitable manner, to the dose setting mechanism housing when the injector pen is assembled by the manufacturer. Alternatively, where the drug delivery device comprises or exhibits a reusable drug delivery device, the cartridge is removable and may be removed from the device without destroying the device. In the drug delivery device 1 illustrated in FIGS. 1-3, the device is illustrated as a disposable drug delivery device. However, those of ordinary skill in the art will recognize that the dose setting mechanism could also be used on reusable drug delivery devices as well, while in the case of a reusable pen, wherein the cartridge holder 2 may be reusable, such that the proximal end can be removably mounted or secured, for example via a threaded, bayonet, or snap fit connection, to a reusable dose setting mechanism having a resettable lead screw.

The previously mentioned removable or replaceable cap 14 is used to cover the cartridge holder 2 extending from the main housing 4. Preferably, the outer dimensions of the replaceable cap 14 are similar to or identical to the outer dimensions of the main housing 4 so as to provide an impression of a unitary whole part hen the replaceable cap 14 is in position covering the cartridge holder 2. In use, the removable cap 14 is removed and a pen needle 16 assembly comprising a double-ended needle mounted in a hub may be screwed or pushed onto the distal end of the cartridge holder or alternatively may be snapped onto this distal end.

Cartridge 8 is of conventional design and defines a medicine-filled reservoir that is closed at its proximal end by the piston 10 that is axially slidably and sealably engaged with the cartridge interior wall to hold the fluid medication within the reservoir. The distal, outlet end of the cartridge reservoir is sealed by a septum 11 held by a cap 13 that is secured to a stepped-down diameter neck portion 15 of the cartridge 8. When pen needle assembly 16 is mounted on the distal end of the cartridge holder 2, the proximal point of injection needle 16 passes through a central opening in the distal end of the cartridge holder 2, an opening in the cap 13, and penetrates the cartridge septum 11 to provide a fluid flow outlet by which medicine within the cartridge reservoir can be dispensed from the distal needle tip during operations of injector pen 1. The fluid medicine cartridge 2 shown and described above is illustrative and not intended to be limiting as other constructions may be employed within the scope of this invention.

Main body 4 of injector pen 1 houses an axially advanceable lead screw 22, a drive nut 23, an inner sleeve 29, a dial link 25, a number sleeve 24, a clutch 26, and a compression spring 27. A dose knob 28 is connected to the dial link 25 and is used to set the dose and then to inject the set dose. Housing or main body 4 is formed from a lightweight material, such as injection molded plastic. The housing 4 may be molded as a single, tubular piece for robustness. A window 51 in the housing near its proximal end can be filled with a magnifying lens that snaps fits to the housing and allows dosage indicating markings (not shown) on the number sleeve 24 to be readily visible during use.

Near the interior distal end of the housing 4 is mounted a mid-body 20 that is formed with an central opening having an inward facing anti-rotation mechanism formed from a pair of diametrically opposed elements or tabs 31 having squared off inward ends that each slidably fit within longitudinal keyways 32 in the lead screw 22. In alternate embodiments, features other than tabs and keyways, for instance a lead screw with flats that fits within a complementarily shaped hole in a collar, may be used to prevent rotation. Tabs 31 prevent the lead screw 22 from rotating within the housing 4 during pen use, but permit the lead screw 22 to be shifted longitudinally, such as in the distal direction toward the cartridge. A snap fit or sonic welding connection of the mid-body 20 to the tubular housing 4 can be used to prevent axial and rotational relative motion of the mid-body to the housing.

The lead screw 22 is in the form of a screw that is axially translatable and rotatably fixed during dosing and injecting. The term "rotatably fixed" shall mean in this context that the lead screw 22 is prevented from rotation during dosing and injecting. The lead screw 22 includes a shaft with a helical threading 33 along its length, which threading 33 is interrupted by the longitudinally extending keyways or grooves 32. A thread stop 34 shown at the proximal end of the threading 33 is provided and is used in preventing the pen from being set by a user to deliver a dose of medicine larger than remains in cartridge 2. Other forms of stopping the screw motion may be substituted within the scope of the invention, for example, the threading at the proximal screw end could stop near the proximal end where it cannot be cammed in, and such solid screw with thread stop better ensures the nut 23 will not be torqued off the screw during dose setting. The distal end of lead screw 22 includes an enlarged, disc-shaped foot or bearing 21 to distribute loading on the cartridge piston 10 that the bearing contacts and thereby directly engages during piston advancing. The separate bearing foot 21 can be attached, such as with a snap fit 20 that may permit relative rotation, to the lead screw 22. The lead screw 22 is shown as being a one-piece plastic injection molding, but alternate materials of construction and multiple pieces are possible.

Figure 4:
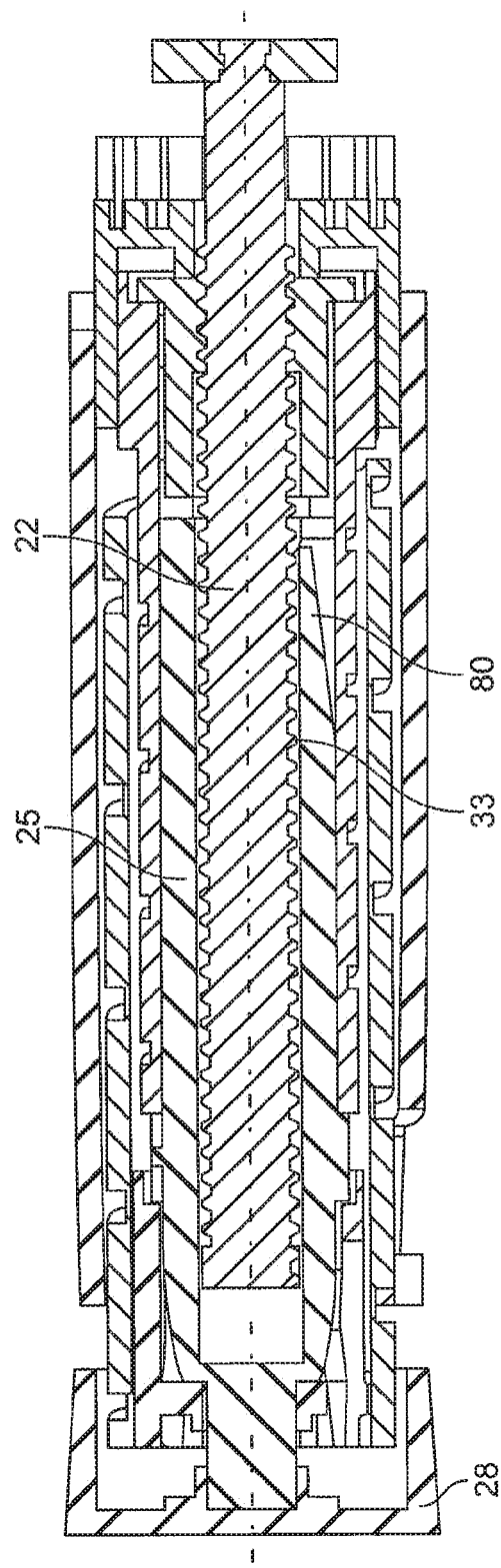
FIG. 4 is a cross-sectional view of one embodiment of the invention where the dial link includes a ratchet arm to engage the threads on the lead screw during both dose setting and dose delivery.

FIGS. 4-6 show one embodiment of the invention where at least one of the dial link fingers 43 has been modified with at least one ratchet arm 80 to engage the threads or threading 33 of the lead screw 22. The ratchet arm 80 is configured to extend radially inward such that it engages the threads 33 to ride up and over each individual thread or winding as the dial link moves axially relative to the lead screw during dose setting and dose injection. As the dial link 25 moves relative to the lead screw 22 during dialing and dispensing, the ratchet arm 80 will snap over the thread 33 of the lead screw 22 generating a clicking sound. The ratchet arm 80 is positioned in a way that it is always in contact with the lead screw thread 33. One such design includes more than one ratchet arm, for example one arm on each of the dial link fingers 43 could be used. As the lead screw 22 moves forward in the distal direction after each subsequent dosing the less and less medicament will remain in the cartridge 8. As the lead screw 22 moves further and further distally into the cartridge 8 there will be less threads available for the ratchet arm 80 to contact during dose dialing and dose dispense. As such, the clicking sound will not be generated over the entire dose setting and dose dispensing sequences.

This is related to the relative movement of the lead screw 22 to the dial link 25 during usage of the pen. Meaning that at the end of the use cycle (a lot of drug is already expelled) the lead screw 22 has moved in distal direction. So the ratchet arm 80 will run over and off the end of the lead screw 22 during dose setting and therefore no longer create the sound. During dispensing the first part of the dosing sequence will run without sound because there is no engagement of the ratchet arm 80 with the lead screw threads 33. However, as the dial link 25 is further advanced distally it will eventually catch up to the remaining threads on the lead screw 22 and the ratchet arm 80 will once again contact or engage the lead screw threads 33 creating the clicking. So the more empty the cartridge 8 is, the more advanced is the lead screw 22 and the shorter is the sound during dose setting and dose dispensing. This gap in the sound (or lack of clicking) works as a signal to the user that the medicament in the cartridge 8 is almost at an end and that a new full cartridge will soon be needed. In other words, the positioning of the ratchet arm 80 along the longitudinal length of the dial link 25 can be selectively chosen so as to customize the audible cartridge fill level or replacement advice feedback signal.

Yet another embodiment of the invention is shown in FIGS. 7-8. Drive nut fingers 36 include a linear row of teeth 82 that run parallel to the longitudinal axis of the drug delivery device. These teeth 82 engage a flexible arm 81 located on the distal end of dial link fingers 43. As the dial link 25 and drive nut 25 move relative to each other during dose setting and injection the flexible arm 81 with run up and down each tooth 82 generating a ratchet sound (clicking) between the drive nut 23 and dial link 25. The ratchet arm 80 is located one the contact surface between both parts. Although the flexible arm 81 is illustrated being on the dial link fingers 43 the reverse could be possible where the teeth are on the dial link and the flexible arm is on the drive nut fingers 36. Another possible configuration of this embodiment would be where there is only one click at the end of the injection providing feed back to the user that the injection was complete. In such a design there would be only one ratchet tooth located in a most distal end of the drive nut finger.

Flexible arms 81 and ratchet arm 80 can be integral with the dial link fingers or they can be a separate component. The configuration of both the arms and ratchet teeth are such that the user hears a noticeable and audible "CLICK" as the arm rides up and over the teeth. Preferably, the design also provides that the user feels or senses a tactile feedback indicating that a dose setting or dose delivery is in progress. The arms can be fabricated from either plastic or metal.

The dial link 25 may comprise a first portion. Said first portion may belong to a feedback ratchet, e.g. to the herein described feedback functionality. The first portion may comprise the ratchet arm 80. Accordingly, the lead screw 22 may comprise a second portion of the feedback ratchet. The thread 33 of the lead screw 22 may be comprised by said second portion (portions not explicitly indicated).

Alternatively, the drive nut 23 may comprise the second portion, wherein the teeth 82 may be comprised by the second portion, wherein either the first portion comprises a ratchet arm and the second portion comprises a, e.g., a single tooth or a linear row of ratchet teeth or the second portion comprises a ratchet arm and the first portion comprises a single tooth or a linear row of ratchet teeth.

Although this is not explicitly indicated, also the inner sleeve 29 may comprises the second portion of the feedback ratchet.

The drive nut 23 includes a cylindrical, tube-shaped body with flexible fingers 36 and clicker teeth 35. The distal region of the drive nut 23 is formed with an internal threading 37 that threadedly engages in a friction locking fashion the threading 33 on the lead screw 22. Threadings 33 and 37 are shown as a double start threading but may be differently formed while still providing suitable friction locking capabilities, such as a single start threading or another multiple start threading. The drive nut 23 is located within the inner sleeve 29 and is axially, but not rotationally fixed, to the inner sleeve 29. In the original commercial design as drive nut 23 is rotated relative to inner sleeve 29 during dose setting, clicker teeth 35 engage in a ratchet fashion flexible arms 38 that project radially on the inside of the inner sleeve 29. As the drive nut 23 rotates the flexible arms 38 ride over the teeth 35 creating an audible clicking noise. Thereby, a setting feedback clicker may be established. The teeth are configured so that each click is equal to one dose volume being set. As few as one flexible clicker arm 38 may be provided, but the use of four equally angularly spaced arms 38 aids in centering drive nut 23 within the inner sleeve 29. However, with our present configuration where a ratchet arm engages the threads on the lead screw or where a flexible arm on one of the dial link and drive nut engage teeth on the other, there is no need to have flexible arms 38 or clicker teeth 35. The hollow interior of drive nut body 23 located proximally of the threading 37 allows free passage of the proximal end of lead screw 22. The exterior surface of drive nut 23 is designed to cooperatively engage with dial link 25 so that the drive link 25 is axially free and rotatably fixed relative to drive nut 23. Thus, during use the dial link 25 is axially moveable relative to, but rotatably locked with, the threaded drive nut. This connection is possible because of the cooperation of the proximally extending fingers 36 on drive nut 23 and the distally extending fingers of the dial link 25. These two sets of fingers 36, 43 move axially relative to each other but engage each other rotationally during dose setting when the dial link 25 is rotated by turning dose knob 28, which is fixed to the dial link 25. The drive nut 23 is shown as being a one-piece plastic injection molding, but other constructions are within the scope of the invention.

In the shown embodiment, the dial link 25 is formed in one piece of an injection molded plastic and which fits within the body 4. A flange 40 that rings a central region of the dial link body includes splines or teeth 39 that extend from the distal face of the flange 40, and teeth 41 that extend from the proximal face of the flange 40. A stepped-down portion of the proximal end of the dial link 25 forms an axially and proximally extending stem 42. The distal end of the dial link body includes the pair of fingers 43 that fit with the fingers 36 of the drive nut 23 to allow axial motion but not rotational motion of the drive nut 23 relative to the dial link 25, thereby rotationally locking the pieces together within the same annular space. Fingers 36 and 43 extend sufficiently axially to ensure they do not disengage during the setting of the maximum pen dose for injection.

An injection molded plastic dose knob 28 with a proximal face, and having a distally facing and centrally located bearing collar and alignment post 55 is provided. Dose knob skirt 50 distally extends from the radial periphery of the dose knob distal face to serve as a grip portion for a user during dose setting. Stem 42 of the of the dial link 25 receives the dose knob alignment post and can be ultrasonically welded within the bearing collar during manufacturing assembly, so as to axially and rotatably fix together the dose knob 28 and dial link 25. The term "rotatably fix" shall mean in this context that any relative rotational movement between the dose knob 28 and the dial link 25 is prevented.

Coaxially mounted around the dial link 25 is the number sleeve 24. The number sleeve 24 has a cylindrical exterior surface 30 with a threading 52 formed as a helical groove that engages a corresponding threading 62 formed on the interior surface of body 4 to threadedly engage the number sleeve 24 to the pen housing. Threadings 52 and 62 are shown as a single start threading but may be differently formed. The threading 62 abuts the end 63 of threading 52 on the number sleeve 24 at the maximum pen dose, assuming the cartridge 8 is sufficiently full for such a maximum dose. A stop surface 64 on the distal end of the outer surface of the number sleeve 24 is positioned in slightly spaced apart relationship with a projecting stop at the zero dose position, and another stop surface is to be abutted by the stop if a user attempts to manually screw the screw element below a zero dose position. A hollow interior 65 of the number sleeve 24 is defined by a cylindrical interior surface provided with a helical threading 67.

The outside diameter of number sleeve 24 is selected such that it can fit inside the dose knob 28. The proximal end region of the number sleeve 24 includes a number of notches 70 and corresponding windows 71 that are alternately spaced around the circumference. The number sleeve 24 includes around its exterior surface 30 suitable indicia of therapeutic dose size as visible through body 4 opening 51. A clutch 26 fits within the open proximal end of the number sleeve 24. Ears 72 on the clutch fit within the notches 70 and the assembly fingers 73 snap lock into windows 71 to axially and rotatably lock the number sleeve 24 and the clutch 26 together during manufacturing of the assembly. A ring of axially extending teeth 54 on the clutch 26 formed in the interior surface of the flange cooperate with the dial link teeth 41 proximally facing on dial link 25.

Disposed between the clutch 26 and the inside portion of the dose knob is the compression or biasing spring 27 that urges the clutch 26 to engage the teeth 41 on the dial link 25. During injection, when a user manually applies a plunging force onto the proximal face of dose knob 28, the spring 27 is elastically compressed, thus disengaging the clutch 26 and the number sleeve 24 from the dial link. The flange teeth 41 on the dial link 25 and clutch teeth 54 mesh when the spring 27 has biased the clutch 26 and the attached the number sleeve 24 to the dose knob 28 and the dial link 25. The dose knob 28 and dial link 25 are not meshed with the clutch 26 and the number sleeve 28 when the spring 27 has been sufficiently compressed during injecting. While a helically coiled metal wire spring is shown, other forms of commonly known biasing elements may be substituted.

The inner sleeve 29 is injection molded from plastic and includes a tubular body that fits into the hollow 65 of the number sleeve 24. The inner sleeve 29 has a helical threading 75 on its outer surface that engages the internal threading 67 on the inside surface of the number sleeve 24. Threadings 67 and 75 are shown as a single start threading, but may be differently formed. The proximal most portion of the end of inner sleeve 24, which end is partially helically shaped corresponding to the threading, is notched to form a partial ring of axially projecting teeth 76 that, when meshed with dial link distally facing teeth 39, serve to rotatably lock together the dial link 25 and the inner sleeve 29. The inner sleeve 29 is keyed to the pen body 4 through the intermediate mid-body 20 that is axially and rotationally fixed to the body 4. The distal end of the inner sleeve 29 has a pair of ridge-defined slots 77 on the periphery of the inner sleeve 24 which axially, slidably receive the lugs 78 radially inwardly projecting from the mid-body 20.

Openings molded into the inner sleeve 29 define four resilient fingers 38 having radially inwardly projecting teeth that are axially oriented and shaped to project into a recess in the distal end of the drive nut 23 that has radially projecting teeth or ridges 35 such that the inwardly projecting teeth click over, in either rotational direction, teeth 35 during dose setting. The fingers 38 with teeth cooperate with the recess on the drive nut 23 to hinder the nut 23 from coming off the inner sleeve 29 after being assembled thereto during manufacture.

To facilitate back-driving during dose delivery, the threaded connections of the number sleeve 24 and the body 4, and the number sleeve 24 and the inner sleeve 29, are non-binding and provided by projecting 60° face angle threads that slide within correspondingly designed recessed grooves. With these threadings, it is preferred that the mechanical advantage is 3.4 or greater, and the screw lead of the drive member or drive nut is 0.108 inch.

The operation of the above described embodiment will now be explained. The pen 1 with a needle 16 attached should first be primed to remove any trap air in the cartridge 8 and to ensure the bearing 21 is in contact with the proximal end of the cartridge stopper or piston 10. In particular, typically while clutching the pen body 4 in one hand, a user manually grips the dose knob skirt 50 and then begins to turn the knob 28 relative to the body 4. At the zero dose arrangement, and as long as knob 28 is not also being plunged which is improper, the knob 28 can only be rotated in a dose increasing direction due to the number sleeve 24 not being further movable distally. A user stops the rotating after a short amount of number sleeve travel that is associated with a small delivery volume, such as one or two units, which is indicated by markings visible through a window 51. Then, and after removing the cap 14 and any other needle cap present, and while pointing the needle tip upward, the user applies a plunging force on the dose knob 28 to drive it distally until the number sleeve 24 returns to the zero dose position, at which the number sleeve threading 52 has reached the distal end of the body threading 62, during which plunging action the piston 10 is shifted forward within cartridge 8. If a user sees that the piston movement has caused liquid to reach the needle distal tip, the priming process is complete. If no liquid is visible at the needle tip, the priming steps are repeated as needed. After priming, the pen 1 is ready to be used for an actual injection.

First, a user prepares the pen by setting the desired dose, as visible in window 51, by turning of knob 28. If the user dials up too large of a dose, and without expelling any medicine, the user can rotate down the dial by turning the knob 28 in the opposite direction, all the way back to zero if desired. To set a dose, the knob 28 is turned in a clockwise direction. Because the dose knob 28 and dial link 25 are fixed rotationally, the dial link 25 is rotated causing the distally facing fingers 43 to engage the proximally facing fingers 36 of the drive nut to thereby turn the drive nut in same direction. Rotation of the drive nut 23 causes the nut 23 to rotate relative to the stationary lead screw 22 whereby the nut 23 moves or climbs up the lead screw 22 in the proximal direction. The drive nut 23 rotates relative to the inner sleeve 29 that is held rotationally fixed relative to the body 4 through the splined connection to the mid-body 20. Because drive nut and inner sleeve are axially fixed, proximal axial movement of the drive nut 23 causes the inner sleeve 29 to slide proximally relative to the mid-body 20. Because the clutch 26 is rotationally fixed with the dial link 25 the clutch 26 rotates causing the number sleeve 24 to rotate and to spin out proximally away from body 4. Because the pitch of the threads on the number sleeve 24 are greater than the pitch of the threads on the inner sleeve 29, the number sleeve 24 and the dial link 25 will translate a larger axially distance compared to the inner sleeve 29 and the drive nut 23.

To inject the dose, after pen 1 is manipulated so the injection needle distal tip properly penetrates, for example, a user's skin, an axial, distal plunging force is applied to the knob face 53 to force the dial link 25 axially in the distal direction toward the body 4, such as with a thumb or index finger of the hand which grasps the housing 4. Initially during injecting, the dial link 25 is shifted axially, which shifting motion compresses the biasing spring 27 to close the gap between the knob surface and the proximal end of the number sleeve 24. The biasing spring 27 is designed to compress prior to the number sleeve 24 moving relative to the body 4. When dial link 25 shifts relative to the number sleeve 24 to the axial arrangement of the drive nut 23, the clutch teeth 54 and dial link teeth 42 disengage to allow a backdriving rotation of the number sleeve 24 relative to the dial ink 25. During the axial movement of the dial link 25, drive nut 23 does not move axially or rotationally. When the number sleeve 24 and the clutch 26 rotatably uncouples from the dial link 25, as the dial link 25 is continued to be axially plunged without rotation by the user by the plunging of the knob 28, the number sleeve 24 screws into the body 4 as it spins relative to the knob 28 and the dose markings on the number sleeve 24 that indicate the amount still remaining to be injected is visible through window 51.

As it screws down, the number sleeve 24 causes inner sleeve 29 to in essence screw up the internal thread inside of the number sleeve threading as the inner sleeve 29 advances distally a lesser distance than the number sleeve 24. The advancement of the inner sleeve 29, due to the abutting or direct engagement with the distal end of the drive nut 23, advances drive nut 23 without rotation, which due to its threaded connection with the lead screw 22 advances the lead screw 22 axially without rotation, which lead screw advancement shifts cartridge piston 10 to expel medication from the cartridge reservoir. The injection is completed when the number sleeve threading 52 has reached the distal end of the body 4, at which time pen 1 is once again arranged in the ready state or zero dose position.

Pen 1 can continue to be used to deliver any desired dose until the medicine remaining in the cartridge 8 is insufficient for a proper dosing. This insufficiency is indicated to the user by the inability to fully set the desired dose due to drive nut threading 37 abutting the thread stop 34 of the lead screw 22, at which time the drive nut 23 and dial link 25 cannot be rotated proximally any farther. When insufficient medicine remains, the pen 1 is to be disposed of and replaced with a similar but entirely new pen.

The terms "medicament" or "medicinal product", as used herein, mean a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des (B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:
H-(Lys)4-des Pro36, des Pro37 Exendin-4(1-39)-NH2,
H-(Lys)5-des Pro36, des Pro37 Exendin-4(1-39)-NH2,
des Pro36 Exendin-4(1-39),
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39),
wherein the group -Lys6-NH2 may be bound to the C-terminus of the Exendin-4 derivative; or an Exendin-4 derivative of the sequence
des Pro36 Exendin-4(1-39)-Lys6-NH2 (AVE0010), H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4 (1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4 (1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4 (1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2, H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp(O2) 25, Asp28] Exendin-4(1-39)-NH2,
des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, Trp(O2)25, Asp28] Exendin-4(S1-39)-(Lys)6-NH2,
H-Asn-(Glu)5-des Pro36, Pro37, Pro38 [Met(O)14, Trp(O2) 25, Asp28] Exendin-4(1-39)-(Lys)6-NH2;
or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region (CH) and the variable region (VH). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H—H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

While this invention has been shown and described as having various designs, the present invention may be modified within the spirit and scope of this disclosure. For example, to deliver a fixed dose, the pen would preferably be modified such that the maximum that the dial could be screwed out to prepare the pen for injection would correspond to the fixed dose. Such a fixed dose pen could eliminate numerical dosage indicating marking, and instead provide user cues in the form of, for example, instructions and a graphical dosing indicator. This disclosure is therefore intended to cover any variations, uses or adaptations of the invention using its general principles. Further, this disclosure is intended to cover such departures from the present disclosure as come within known or customary practice in the art to which this invention pertains.

The invention claimed is:

1. An assembly for a drug delivery device, the assembly comprising:
    a housing;
    a lead screw having a longitudinal axis, a distal end, and a proximal end, the lead screw being rotatably fixed during dose setting and dose delivery and axially movable in a distal direction relative to the housing, the lead screw further including a thread;
    a drive nut threadedly engaged with and screwable along the thread of the lead screw;
    a dial link connected with the drive nut and axially movable and rotatably fixed relative to the drive nut, where the dial link comprises a first portion of a feedback ratchet, and wherein the assembly is configured such that,
        during dose setting, the dial link is moved relative to the housing a first axial distance from a home position and the drive nut is moved along the thread of the lead screw a second axial distance, and
        during dose delivery, the dial link is moved relative to the housing back toward the home position, and the drive nut and therewith the lead screw is advanced axially; and
    a second portion of the feedback ratchet, wherein the second portion is arranged and configured to engage the first portion of the feedback ratchet such that, during dose delivery, contact between the first portion of the feedback ratchet and the second portion of the feedback ratchet generates a feedback signal, where the drive nut comprises the second portion of the feedback ratchet.

2. The assembly of claim 1, where one of the first portion of the feedback ratchet and the second portion of the feedback ratchet comprises a ratchet arm configured to engage the other of the first portion of the feedback ratchet and the second portion of the feedback ratchet.

3. The assembly of claim 1 where the second portion of the feedback ratchet is arranged and configured to engage the first portion of the feedback ratchet such that, during dose setting, the contact between the first portion of the feedback ratchet and the second portion of the feedback ratchet generates another feedback signal separate from the feedback signal.

4. The assembly of claim 1, wherein either the first portion of the feedback ratchet comprises a ratchet arm and the second portion of the feedback ratchet comprises a row of ratchet teeth or the second portion of the feedback ratchet comprises the ratchet arm and the first portion of the feedback ratchet comprises the row of ratchet teeth.

5. The assembly of claim 1, where a portion of the first portion of the feedback ratchet and the second portion of the feedback ratchet not comprising a ratchet arm comprises a single ratchet tooth, where the first portion of the feedback ratchet and the second portion of the feedback ratchet are positioned such that only one end-of-dose feedback signal is generated when a preset dose has been fully dispensed.

6. The assembly of claim 1, comprising an inner sleeve, wherein the inner sleeve is axially fixed relative to the drive nut, and wherein the inner sleeve is rotatably fixed with respect to the housing.

7. The assembly of claim 6, wherein the assembly is configured such that the drive nut is rotatable with respect to the inner sleeve and a setting feedback clicker mechanism is established between the inner sleeve and the drive nut during dose setting, and wherein the setting feedback clicker mechanism generates a further feedback signal.

8. The assembly of claim 1, comprising a number sleeve which is threadedly engaged with the housing, wherein the assembly is further configured such that, during dose setting, the dial link is rotatably fixed with the number sleeve when the dial link and number sleeve are in a first axial arrangement, and, during dose delivery, the number sleeve is rotatable relative to the dial link when the dial link and the number sleeve are in a second axial arrangement.

9. The assembly of claim 8, comprising an inner sleeve, wherein the inner sleeve is axially fixed relative to the drive nut, and wherein the inner sleeve is rotatably fixed with respect to the housing, wherein the assembly is configured such that the inner sleeve is threadedly engaged with the number sleeve, and wherein, during dose delivery, the inner sleeve advances the drive nut axially.

10. A drug delivery device comprising the assembly of claim 1.

11. An assembly for a drug delivery device, the assembly comprising:
    a housing;

a lead screw having a longitudinal axis, a distal end, and a proximal end, the lead screw being rotatably fixed during dose setting and dose delivery and axially movable in a distal direction relative to the housing, the lead screw further including a thread;

a drive nut threadedly engaged with and screwable along the thread of the lead screw;

a dial link connected with the drive nut and axially movable and rotatably fixed relative to the drive nut, where the dial link comprises a first portion of a feedback ratchet, and wherein the assembly is configured such that, during dose setting, the dial link is moved relative to the housing a first axial distance from a home position, and the drive nut is moved along the thread a second axial distance, and during dose delivery, the dial link is moved relative to the housing back toward the home position, and the drive nut and therewith the lead screw is advanced axially;

a second portion of the feedback ratchet, wherein the second portion is arranged and configured to engage the first portion of the feedback ratchet such that, during dose delivery, contact between the first portion of the feedback ratchet and the second portion of the feedback ratchet generates a feedback signal; and an inner sleeve, wherein the inner sleeve is axially fixed relative to the drive nut, and wherein the inner sleeve is rotatably fixed with respect to the housing.

12. An assembly for a drug delivery device, the assembly comprising:

a housing;

a lead screw having a longitudinal axis, a distal end, and a proximal end, the lead screw being rotatably fixed during dose setting and dose delivery and axially movable in a distal direction relative to the housing, the lead screw further including a thread;

a number sleeve which is threadedly engaged with the housing;

a drive nut threadedly engaged with and screwable along the thread of the lead screw;

a dial link connected with the drive nut and axially movable and rotatably fixed relative to the drive nut, where the dial link comprises a first portion of a feedback ratchet, and wherein the assembly is configured such that, during dose setting, the dial link is moved relative to the housing a first axial distance from a home position, the drive nut is moved along the thread a second axial distance, and the dial link is rotatably fixed with the number sleeve when the dial link and number sleeve are in a first axial arrangement, and during dose delivery, the dial link is moved relative to the housing back toward the home position, the drive nut and therewith the lead screw is advanced axially, and the number sleeve is rotatable relative to the dial link when the dial link and the number sleeve are in a second axial arrangement; and a second portion of the feedback ratchet, wherein the second portion is arranged and configured to engage the first portion of the feedback ratchet such that, during dose delivery, contact between the first portion of the feedback ratchet and the second portion of the feedback ratchet generates a feedback signal.

\* \* \* \* \*